: US010921056B2

United States Patent
Weber et al.

(10) Patent No.: US 10,921,056 B2
(45) Date of Patent: *Feb. 16, 2021

(54) COATED MEDICAL DEVICES AND METHODS FOR DRYING COATED MEDICAL DEVICES

(71) Applicant: BOSTON SCIENTIFIC SCIMED, INC., Maple Grove, MN (US)

(72) Inventors: Jan Weber, Maastricht (NL); Bruce R. Forsyth, Hanover, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/236,239

(22) Filed: Dec. 28, 2018

(65) Prior Publication Data

US 2019/0137177 A1 May 9, 2019

Related U.S. Application Data

(63) Continuation of application No. 15/094,285, filed on Apr. 8, 2016, now Pat. No. 10,184,719.

(Continued)

(51) Int. Cl.
| | |
|---|---|
| *B05D 3/02* | (2006.01) |
| *F26B 3/347* | (2006.01) |
| *A61L 31/16* | (2006.01) |
| *A61L 27/54* | (2006.01) |
| *A61L 31/06* | (2006.01) |
| *A61L 31/10* | (2006.01) |

(52) U.S. Cl.
CPC .............. *F26B 3/347* (2013.01); *A61L 27/54* (2013.01); *A61L 31/06* (2013.01); *A61L 31/10* (2013.01); *A61L 31/16* (2013.01); *B05D 3/029* (2013.01); *A61L 2300/416* (2013.01); *A61L 2300/606* (2013.01); *A61L 2300/63* (2013.01); *A61L 2420/02* (2013.01); *B05D 2201/00* (2013.01); *B05D 2202/00* (2013.01)

(58) Field of Classification Search
None
See application file for complete search history.

(56) References Cited

U.S. PATENT DOCUMENTS 5,521,360 A * 5/1996 Johnson ................ H05B 6/686
219/709
5,725,572 A 3/1998 Lam et al.
(Continued)

OTHER PUBLICATIONS

Bhat et al., "Microwave Radiations for Heat-Selling of Polyester Fibers," Journal of Engineered Fibers and Fabrics, 4(4):1-6, 2009.

*Primary Examiner* — Cachet I Proctor
(74) *Attorney, Agent, or Firm* — Seager, Tufte & Wickhem, LLP

(57) ABSTRACT

Medical devices and methods for drying medical devices are disclosed. An example method for drying a medical device may include disposing a medical device within a drying apparatus. The drying apparatus may include a variable frequency microwave heating device. The medical device may include a substrate, the substrate including an active pharmaceutical ingredient and a solvent. The method may also include heating the medical device with the drying apparatus. Heating may evaporate at least a portion of the solvent.

19 Claims, 8 Drawing Sheets

Related U.S. Application Data

(60) Provisional application No. 62/145,473, filed on Apr. 9, 2015, provisional application No. 62/220,700, filed on Sep. 18, 2015.

(56) References Cited

U.S. PATENT DOCUMENTS

| | | | |
|---|---|---|---|
| 7,211,150 B1 * | 5/2007 | Kokish | B05B 13/0242 |
| | | | 118/320 |
| 8,637,109 B2 | 1/2014 | Grewe et al. | |
| 8,795,761 B2 * | 8/2014 | Bobson | F26B 21/004 |
| | | | 118/58 |
| 2003/0183966 A1 * | 10/2003 | Wang | B29C 48/908 |
| | | | 264/40.1 |
| 2003/0183972 A1 | 10/2003 | Weber et al. | |
| 2003/0234459 A1 * | 12/2003 | Nandu | B29C 35/0288 |
| | | | 264/1.36 |
| 2005/0196518 A1 * | 9/2005 | Stenzel | A61L 31/10 |
| | | | 427/2.1 |
| 2006/0030936 A1 | 2/2006 | Weber et al. | |
| 2006/0047336 A1 | 3/2006 | Gale et al. | |
| 2008/0102192 A1 | 5/2008 | Johnson et al. | |
| 2009/0043276 A1 * | 2/2009 | Weber | A61F 2/88 |
| | | | 604/502 |
| 2009/0181156 A1 * | 7/2009 | Nesbitt | A61L 31/10 |
| | | | 427/2.1 |
| 2011/0130829 A1 * | 6/2011 | Clarke | A61L 27/30 |
| | | | 623/1.42 |
| 2012/0128863 A1 | 5/2012 | Nguyen et al. | |
| 2013/0071549 A1 * | 3/2013 | Chen | F26B 25/066 |
| | | | 427/2.25 |

* cited by examiner

COATED MEDICAL DEVICES AND METHODS FOR DRYING COATED MEDICAL DEVICES

CROSS-REFERENCE TO RELATED APPLICATIONS

This application is a continuation of U.S. application Ser. No. 15/094,285, filed Apr. 8, 2016; which claims the benefit of priority under 35 U.S.C. § 119 to U.S. Provisional Application Ser. No. 62/220,700, filed Sep. 18, 2015, and U.S. Provisional Application Ser. No. 62/145,473, filed Apr. 9, 2015, the entire disclosures of which are incorporated herein by reference.

TECHNICAL FIELD

The present disclosure pertains to medical devices, and methods for manufacturing medical devices. More particularly, the present disclosure pertains to coated medical devices and methods for drying coated medical devices.

BACKGROUND

A wide variety of intracorporeal medical devices have been developed for medical use, for example, intravascular use. Some of these devices include guidewires, catheters, stents, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example method for drying a medical device is disclosed. The method comprises:

disposing a medical device within a drying apparatus;

wherein the drying apparatus includes a variable frequency microwave heating device;

wherein the medical device includes a substrate, the substrate including an active pharmaceutical ingredient and a solvent; and heating the medical device within the drying apparatus, wherein heating evaporates at least a portion of the solvent.

Alternatively or additionally to any of the embodiments above, the medical device includes a metallic stent.

Alternatively or additionally to any of the embodiments above, the medical device includes a polymeric stent.

Alternatively or additionally to any of the embodiments above, the variable frequency microwave heating device is designed to heat across a frequency band of 300 MHz to 40 GHz.

Alternatively or additionally to any of the embodiments above, heating the medical device within the drying apparatus includes cycling the variable frequency microwave heating device across the frequency band.

Alternatively or additionally to any of the embodiments above, cycling occurs at a fixed power input.

Alternatively or additionally to any of the embodiments above, cycling occurs at a cycle time of 10-500 ms.

Alternatively or additionally to any of the embodiments above, cycling occurs at a cycle time of 10-500 ms with a duty cycle of 1% to 99%.

Alternatively or additionally to any of the embodiments above, the variable frequency microwave heating device monitors the temperature of the medical device and modulates the frequency based on the temperature of the medical device.

Alternatively or additionally to any of the embodiments above, the variable frequency microwave heating device monitors the temperature of the medical device and modulates the process parameters in terms of duty cycle, frequency or/and power level, based on the temperature of the medical device.

Alternatively or additionally to any of the embodiments above, the substrate includes poly-L-lactic acid, poly-D-lactic acid, a racemic mixture of poly-L-lactic acid and poly-D-lactic acid, poly(lactic-co-glycolic acid), or combinations thereof.

Alternatively or additionally to any of the embodiments above, the active pharmaceutical ingredient includes everolimus, paclitaxel, or combinations thereof.

Alternatively or additionally to any of the embodiments above, heating the medical device with the drying apparatus defines a plurality of hydrophilic regions along the substrate.

Alternatively or additionally to any of the embodiments above, heating the medical device with the drying apparatus forms a plurality of micro-channels in the substrate.

Alternatively or additionally to any of the embodiments above, further comprising cooling a section of the medical device while heating the medical device with the drying apparatus.

An example medical device is disclosed. The medical device comprises:

an implantable medical device having a coating disposed thereon;

an active pharmaceutical ingredient disposed within the coating; and wherein the coating is applied to the medical device and dried using a variable frequency microwave drying apparatus so that the coating defines a plurality of hydrophilic regions.

Alternatively or additionally to any of the embodiments above, the coating has a substantially uniform crystal structure.

Alternatively or additionally to any of the embodiments above, the coating has a plurality of micro-channels formed therein.

An example method for drying a medical device is disclosed. The method comprises:

disposing a medical device within a variable frequency microwave heating device;

wherein the variable frequency microwave heating device is designed to heat across a frequency band of 300 MHz to 40 GHz;

wherein the medical device includes a polymeric material and a solvent;

heating the medical device with the variable frequency microwave heating device, wherein heating evaporates at least a portion of the solvent; and wherein heating the medical device with the variable frequency microwave heating device includes cycling the variable frequency microwave heating device across the frequency band.

Alternatively or additionally to any of the embodiments above, heating the medical device with the variable frequency microwave heating device includes cycling the variable frequency microwave heating device across the frequency band, and cycling occurs at a fixed power input and cycling occurs at a cycle time of 10-500 ms.

Alternatively or additionally to any of the embodiments above, the medical device includes a polymeric stent.

Alternatively or additionally to any of the embodiments above, the medical device includes a drug coated stent.

An example medical device is disclosed. The medical device comprises:

a polymeric shaft having one or more discrete sections exposed to microwave energy from a variable frequency microwave device.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
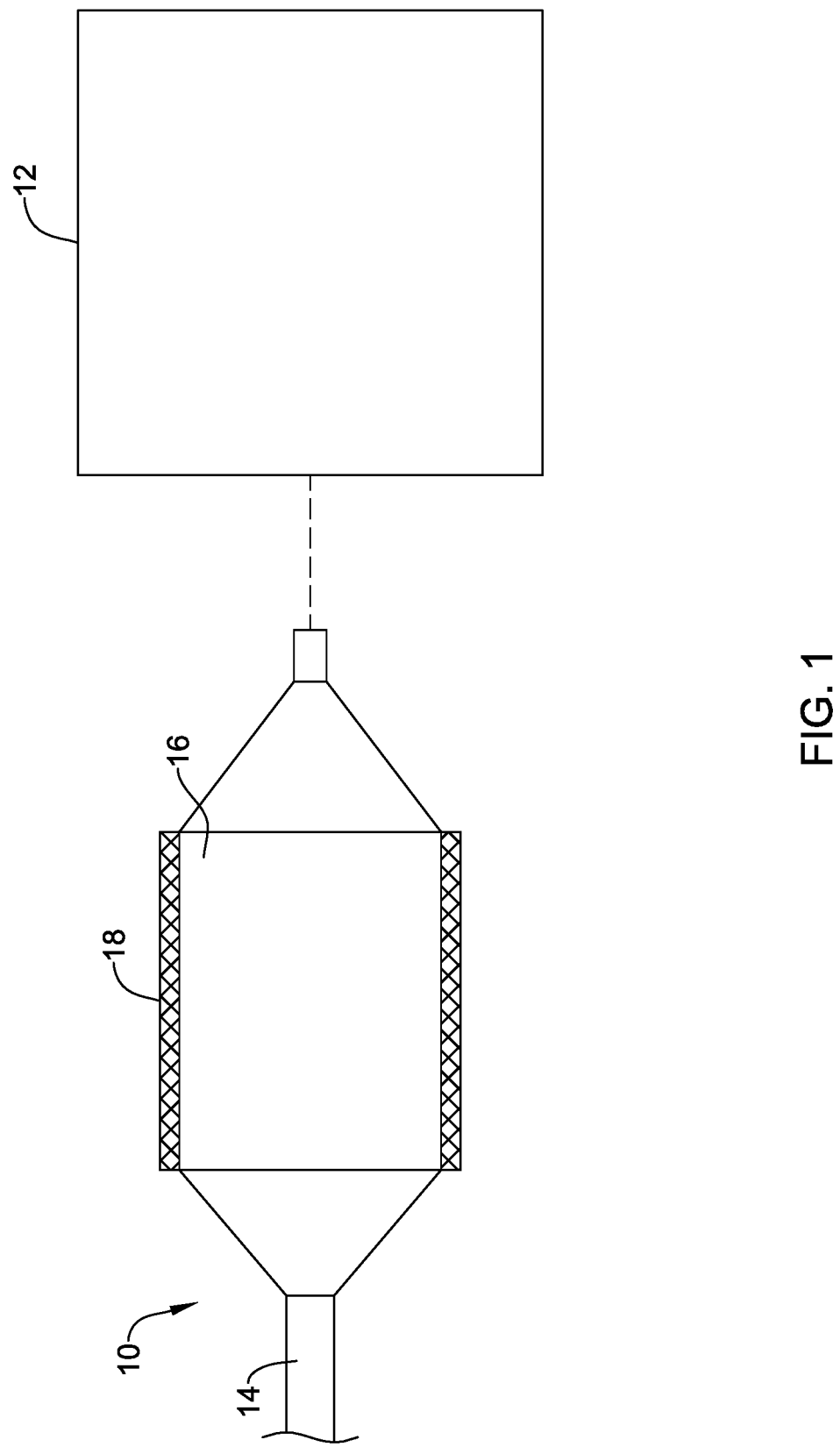
FIG. 1 schematically illustrates an example drying process.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of different medical devices (e.g., catheters, guidewires, stents, etc.) may include coatings. After the coating is applied to a surface of the medical device, a heating process may be used to "dry" the coating. More particularly, a heating process may be used to heat the coating material to drive surface and bulk diffusion of residual solvents into the gas phase for evaporation. Similar drying processes may also be used for medical devices formed from polymers. A typical drying process may use a hot air conduction oven or a convection oven. While effective, the use of such ovens may require relatively long drying times (e.g., 1-6 hours or more). Furthermore, if the drying process does not eliminate all of the solvent, residual solvent in the coating or the medical device itself can impact stability of the coating/device, degrade the polymer material, degrade other components (e.g., active pharmaceutical ingredients), or the like. Furthermore, conventional drying processes may not uniformly heat and, instead, may tend to heat the outer surfaces more than the material as a whole. This could impact the outer surface of the coating/device as well as impact the properties of the coating/device.

Disclosed herein are methods for drying medical devices and/or coatings that are aimed at providing efficient drying while having less impact on the device/coating material. In addition, the drying processes disclosed herein may also provide desirable features or characteristics to the coatings/devices themselves. Thus, medical devices and coatings are disclosed that may have desirable features. Some additional details of these drying processes and medical devices dried using these processes are disclosed herein.

FIG. 1 schematically illustrates a drying process where a medical device 10 is dried using a variable frequency microwave heating device 12. In this example, medical device 10 is a balloon catheter including a catheter shaft 14, a balloon 16 coupled to shaft 14, and a stent 18 disposed along balloon 16. However, a variety of other medical devices are contemplated including polymeric stents, metal stents, drainage stents, grafts, ceramic devices such as orthopedic implants and dental devices, and the like. This process may also be useful for drying and surface modulating polymeric materials as used for artificial aortic and mitral leaflets in artificial valves Microwave heating device 12 (e.g., and/or microwave heating devices in general) heats based on the resistive loss of continuous rotating polar molecular groups or molecules caused by an alternating electric field. Rotating molecules push, pull, and collide with other molecules or molecular groups (through electrical forces), distributing the kinetic energy to adjacent molecules and atoms in the material. Once distributed, this energy appears as heat. The heat may be used to dry medical device 10 and/or components thereof, dry coatings on medical device 10 and/or components thereof (including the evaporation of fluids and/or solvents), facilitate polymerization, or the like.

Energy absorption of molecular groups depends on many factors including the resonance frequencies of the groups in their molecular environment. For example, water in a frozen condition absorbs best at around 1 gigahertz (GHz), in the fluid phase at around 2.45 GHz, and in the vapor phase at about 10 GHz. Because of this, microwave ovens that are used to heat food operate at a single frequency in the S-band of microwave energy (2-4 GHz). However, heating of molecules can occur outside this band.

As indicated above, microwave heating device 12 is a variable frequency microwave heating device. Variable frequency microwave heating device 12 is designed to heat by providing a substantially homogenous field density in the processing region of interest to control the thermal impact on the material products through rapid sweeping of the frequency bandwidth. This may include heating across frequencies in the microwave bands such as the L band (e.g., 1-2 GHz), the S band (e.g., 2-4 GHz), the C band (e.g., 4-8 GHz), the X band (e.g., 8-12 GHz), the K band (e.g., 12-40 GHz), the Q band (e.g., 33-50 GHz). In general, variable frequency microwave heating device 12 may be designed to heat across frequencies ranging from about 300 megahertz (MHz) to 50 GHz or more or about 300 MHz to 40 GHz. The switching of frequencies may also occur at relatively short time intervals. For example, frequency switches may occur at time intervals on the order of about 10-500 microseconds (ms), or about 50-25 ms, or about 100 ms. These are just examples. Other time intervals are contemplated. Variable frequency microwave heating device 12 may deliver energy at a power of about 50-350 watts (W), about 100-300 W, or about 100-200 W. In some instances, the power may be constant. However, variability in power levels are contemplated.

In some instances, variable frequency microwave heating device 12 may simply deliver microwave energy that varies between just two frequencies. For example, simply switching between two frequencies may help to reduce sparks and/or have other desirable benefits. It may also be possible to switch between a single frequency and "off" (e.g., where the power is set to 0). In other instances, variable frequency microwave heating device 12 may deliver microwave energy that varies across more than two frequencies. In some of these and in other instances, variable frequency microwave heating device 12 may deliver microwave energy that varies across a portion or all of the band of frequencies disclosed herein.

Variable frequency microwave heating device 12 may also include temperature sensors that may be used, for example, to monitor heating. For example, variable frequency microwave heating device 12 may include non-contact (e.g., infrared) thermal sensors, thermocouples, fiber optic probes, or the like to monitor the heating process. In at least some instances, the temperature readings may be used to modulate some or more of the process parameters, such as duty cycle, frequency bands, and/or power level. In some of these and in other instances, temperature feedback may also be utilized to modulate power. Additionally or alternatively, a cooling apparatus may be used in conjunction with variable frequency microwave heating device 12 to selectively cool a region (or all) of medical device 10 during the heating/drying process. This may include the use of a cooling gas that may cool medical device 10 to a low temperature (including temperatures below zero degrees Celsius). Additionally or alternatively, variable frequency microwave heating device 12 may include fan, ventilation system, vacuum, or the like that forces air/gases to flow within variable frequency microwave heating device 12. This may include a system that infuses an inert gas into variable frequency microwave heating device 12, which may help to reduce oxidation. A vacuum (e.g., and/or the use of controlled air flow across the material) may also help with solvent removal. Additional fixtures can be used to isolate parts of medical device 10 from heating such as microwave-shielding materials such as metallic foils. Very low dielectric loss materials (microwave-transparent), such as polyetherimide (e.g., ULTEM), polytetrafluoroethylene, ceramics, high density polyethylene, or the like, can be used to mount or support the device in the microwave oven without affecting the electric field.

The use of variable frequency microwave heating device 12 may be desirable for a number of reasons. For example, the long emission wavelength of microwave energy can limit degradation of most polymers and/or drugs if resistive thermal heating can be minimized or otherwise more uniformly distributed. Unlike the photon energy in laser processes causing electrons to jump between energy states, the energy of the electric field in microwaves is not sufficient to cause changes in the electron energy-level distribution in non-metallic materials. In other words, microwave heating does not cause a chemical reaction (e.g., does not directly cause a reaction) unless the amount of heating that occurs leads to the reaction. Controlling the power of variable frequency microwave heating device 12 may also help to reduce unwanted chemical reactions and/or degradation of polymer materials. For example, some polymers such as poly (D,L-lactide) may begin to degrade when microwave energy is delivered at relatively high power levels such that the local temperature rises, e.g. 10 degrees Celsius, above the melting temperature. The use of variable frequency microwave heating device 12 may also affect the molecular vibrational and rotational motion of the solvent molecules based on the material's dielectric constant. Rapid quenching of residual organic solvents or moisture can thereby strengthen and preserve the longevity of many mechanical properties of a medical device (e.g., including polymer tubes, shafts, wires, and the like) that may aid in the retention of certain crystalline or amorphous structures that would be beneficial depending on device requirements.

Variable frequency microwave heating device 12 may be powered at a constant power. Alternatively, variable frequency microwave heating device 12 may use different or a variable amount of power. For example, when referring to the maximum power of the microwave generator, variable frequency microwave heating device 12 may have a power of 1 Watt to 100 kWatts, or about 10 Watts to 10 kWatts. These are just examples. The power of variable frequency microwave heating device 12 may also be referred to in terms of the substrate being heated (e.g., Watts per unit mass of the substrate). As still another alternative, the power of variable frequency microwave heating device 12 may also be referred to in terms of power per unit volume of variable frequency microwave heating device 12 itself. In these instances, variable frequency microwave heating device 12 may have a power of about 1 Watt/liter to 10 kWatts/liter, or about 10 Watts/liter to 1 kWatt/liter.

Variable frequency microwave heating device 12 may also use a "pulsed power" that may allow variable frequency microwave heating device 12 to be run at or near a maximum power level until a pre-determined condition or temperature is reached in the heated device, and then power may be turned off to allow the heated device to cool. Power may then be turned back on and the cycle may be repeated. This may allow for the temperature of the heated device to be controlled more precisely. The use of a pulsed approach may also allow a more rapid and high overall energy transfer efficiency to the device while keeping its temperature at a low level. Low duty cycles and cycle times (e.g., <10% and on the order of seconds) at high power setting and temperature may enable more efficient solvent coupling and mass transfer without affecting other substrate properties (e.g., polymer lamella structure, which may change near the glass transition temperature).

Variable frequency microwave heating device 12 can also be used to dry coating on metallic substrates. This is because in a fixed frequency microwave field, standing waves may be formed that could lead to sparks between the metallic ends of the substrate. Sparks may be reduced by connecting the metal substrate to the wall of the oven (e.g., so the electromagnetic field is grounded). However, such a practice may not completely eliminate sparking. For example, the ends (e.g., sharp ends) of the metal substrate may still be present and may be a region where sparking may still occur. Shifting the frequency (e.g., continuously shifting the frequency) over a band can help to reduce or otherwise eliminate standing waves and, thus, sparking. Therefore, variable frequency microwave heating device 12 can also be used to dry devices that include or are otherwise formed from a metal.

In addition, when relatively low volatility solvents are used in a coating/device, the drying time in a conventional oven may be relatively long (e.g., 1-6 hours or more). Furthermore, if the drying process is inefficient, remaining solvent in the coating or device can affect the mechanical stability (e.g., due to chain scissioning of the base oligomers). The use of variable frequency microwave heating device 12 allows for more efficient drying over a shorter period of time. This not only saves time, it also allows for more efficient removal of solvents, which can desirably impact the stability of the coating/device.

Conventional drying processes may also have a tendency to heat the outer surface or "skin" of the coating first. This could lead to a closing off of the outer surface of the material, which could impact the ability of solvent to escape during drying. In addition, the use of a conventional drying process and/or a fixed frequency microwave can also lead to non-uniform heating (e.g., because fixed frequency microwaves may have a non-uniform field density). In other words, heating in a conventional oven or fixed frequency microwave could lead to hot and cold spots through the heated material. The use of variable frequency microwave heating device 12 allows the target coating/device to be heated more uniformly. In other words, heat is distributed throughout the bulk of the coating/device material itself rather than along the surface.

Microwave drying can also result in more hydrophilic surfaces. This may be desirable for medical devices and/or coatings. Because variable frequency microwave heating device 12 distributes heat more effectively and uniformly through the bulk of the coating/device material compared to the surface, a temperature gradient may be formed that extends toward the surface, which may create a pressure gradient of the solvent (and/or volatile material). This may result in a forced escape of the solvent forming micro-channels in the material that extend from the bulk (e.g., middle) toward the outer surface, resulting in a more hydrophilic surface. In addition, the formation of micro-channels may also define regions where a substance disposed in the coating/device (e.g., including a drug, or the like) could be more efficiently released. This may also allow particles (and/or drugs, molecules, or the like) to be added to a coating after applying a coating. This may be a useful, for example, in case the drug molecule is sensitive to the solvent being used to spray the coating. In addition, this may allow for improved binding of the particles/drug to the coating and/or improved drug release. In some instances, embolic beads (e.g., for use in oncology applications) could be manufactured with pre-defined micro-channels. This may include spraying embolic particles (e.g., using an ultrasonic or other suitable nozzle) within the microwave field, allowing the particles to dry relatively fast and creating micro-channels extending from the bulk (e.g., middle) of the embolic particle toward the outer surface.

Figure 2:
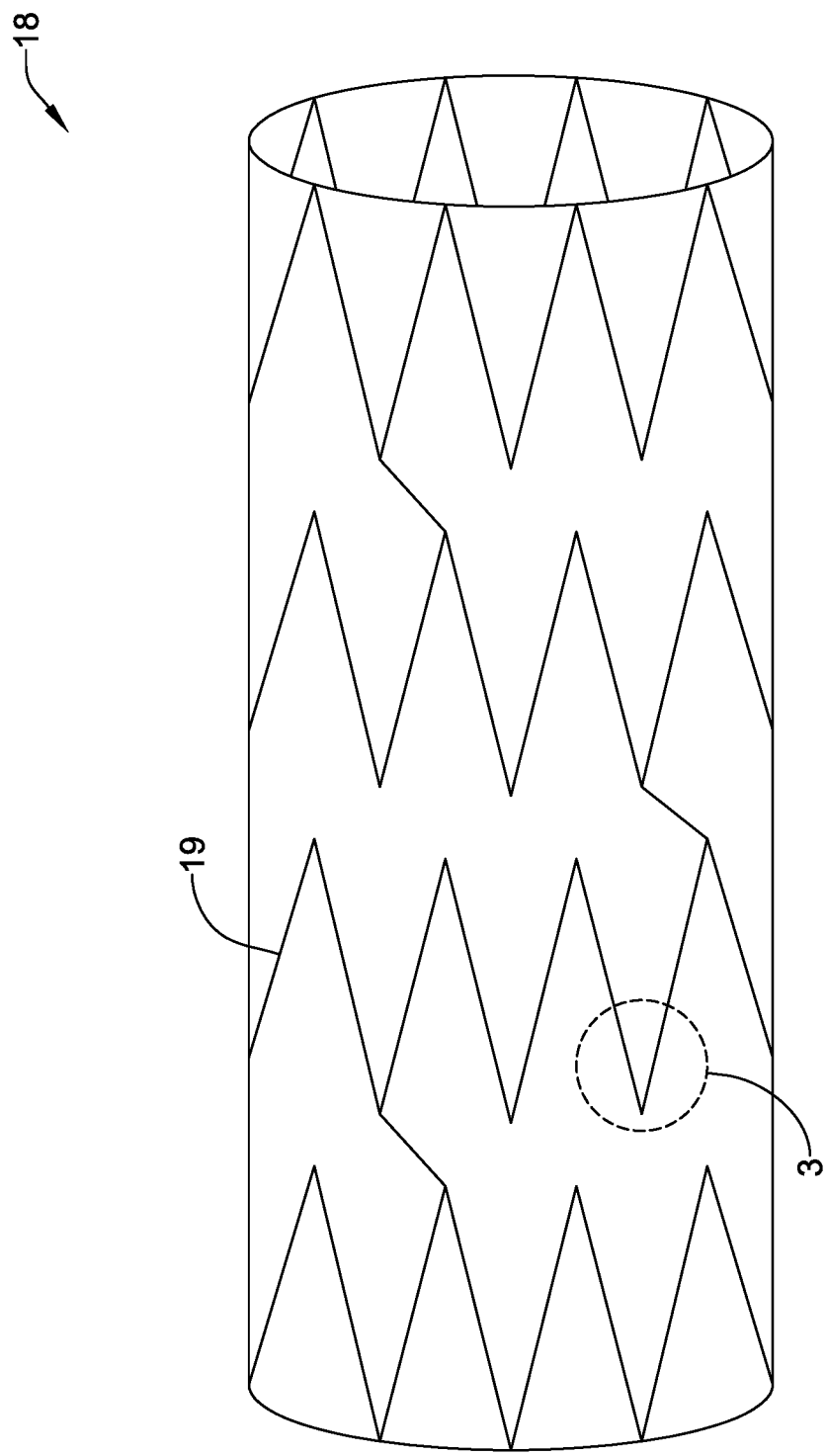
FIG. 2 is a side view of an example medical device.

FIG. 2 illustrates stent 18. In at least some instances, stent 18 is a polymeric stent. In some of these and in other embodiments, stent 18 is a bioabsorbable stent. For example, stent 18 may include a base or substrate 19 that is made from or otherwise includes poly-L-lactic acid, poly-D-lactic acid, a racemic mixture of poly-L-lactic acid and poly-D-lactic acid, poly(lactic-co-glycolic acid), combinations thereof, or the like. Stent 18 may also include an active pharmaceutical ingredient such as, for example, everolimus, paclitaxel, combinations thereof, or the like.

Figure 3:
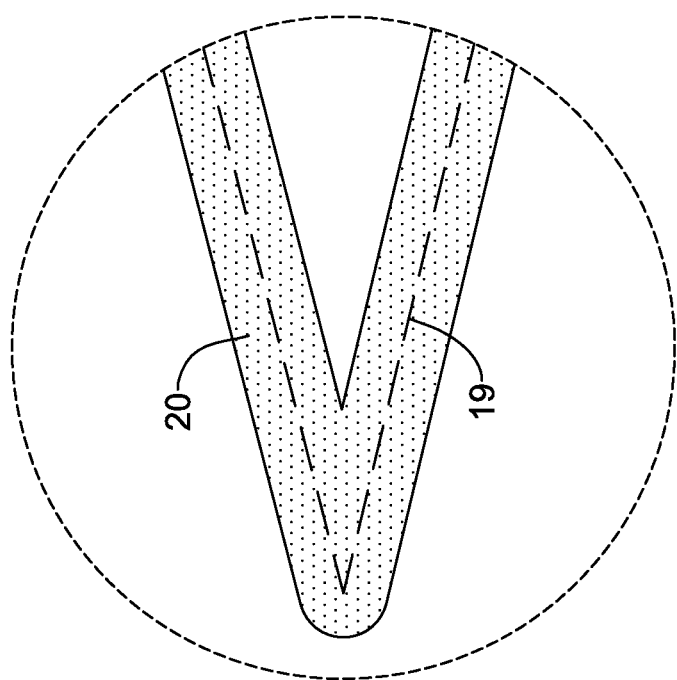
FIG. 3 schematically illustrates a portion of an example medical device.

In some instances, stent 18 may include a coating 20 as shown in FIG. 3. For example, substrate 19 could be a polymeric or metallic scaffold that is coated with coating 20. In some instances, coating 20 can be disposed along only the abluminal surface of substrate. However, in other instances, the adluminal or both the abluminal/adluminal surfaces may include coating 20. Coating 20 may include an active pharmaceutical ingredient such as, for example, everolimus, paclitaxel, combinations thereof, or the like.

Figure 5:
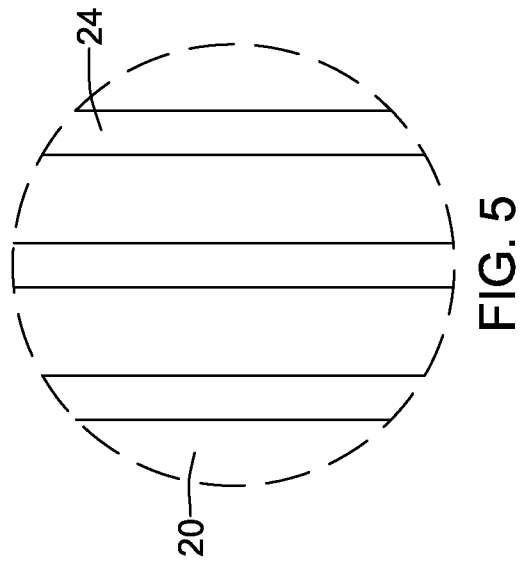
FIG. 5 schematically illustrates a portion of an example medical device.
Figure 6:
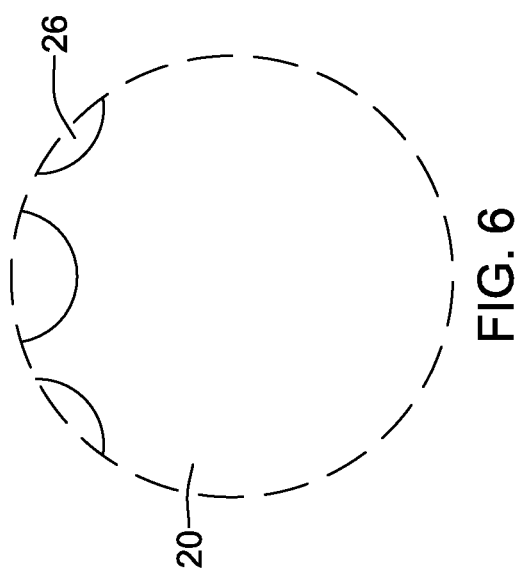
FIG. 6 schematically illustrates a portion of an example medical device.
Figure 4:
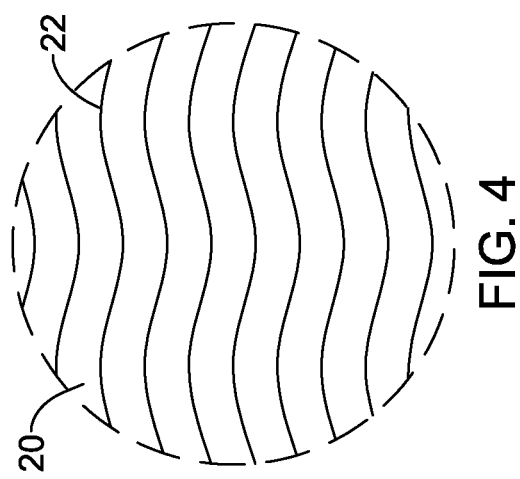
FIG. 4 schematically illustrates a portion of an example medical device.

Some desirable features of stent 18 as a result of the microwave drying process are schematically shown in FIGS. 4-6. For example, the microwave drying process may result in a substantially uniform or otherwise improved crystal structure (e.g., including crystals 22) and/or glass transition temperature in coating 20 as schematically represented in FIG. 4. This differs from conventional thermal oven drying processes that may have greater variability in the impact on the crystal structure. The percent of crystallinity in coating 20 may also be increased relative to conventional drying processes. In general, crystal formation is the result of molecules aligning closely parallel to each other creating various chemical bonds, such as hydrogen-bonds. As the polar groups on molecules in the microwave field are forced to move simultaneously in the same direction, one gets an increased chance of close parallel alignment. Conversely, during conventional heating the molecules tend to randomly move/align. In other words, the chance of parallel molecular alignment may be increased by using microwaves. By sing intermittent short pulsed microwaves, a high degree of orientation can be achieved while limiting the overall heating of the material, which may be desirable, particularly for sensitive materials.

The drying process may result in a plurality of micro-channels 24 in coating 20 as schematically represented in FIG. 5. The drying process may result in a plurality of hydrophilic regions 26 along coating 20 as schematically represented in FIG. 6. These are just examples. In some instances, the microwave drying process can result in any one of these (and other) properties, any combination of these properties, all of these properties, or the like.

Figure 7:
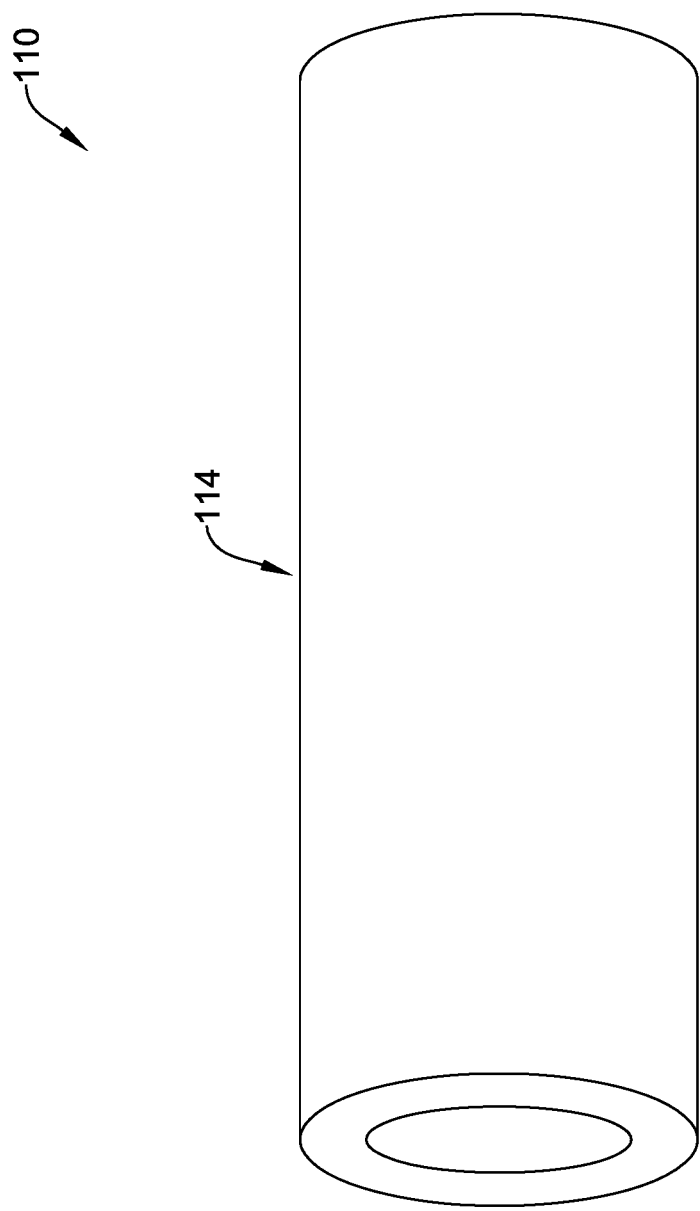
FIG. 7 schematically illustrates a portion of an example medical device.

FIG. 7 illustrates a portion of an example medical device 110 that may be similar in form and function to other medical devices disclosed herein. In this example, device 110 includes a shaft 114 that is depicted as a tubular member. Shaft 114 may be a component of a medical device or may be a tubular medical device (e.g., a catheter). In other instances, shaft 114 may be a solid structure or device (e.g., a stent, a guidewire, and/or the like). Shaft 114 may be formed from a polymeric material such as those polymeric materials disclosed herein. In some instances it may be desirable to modify the structure along shaft 114. For example, portions of shaft 114 may be locally exposed to microwave radiation (e.g., using a variable frequency microwave device as disclosed herein) such that the material of shaft 114 is crystallized (and/or the crystal structure is altered) along the exposed regions to create local changes in mechanical characteristics such as increased stiffness, increased pushability, increased kink resistance, etc. These changes in mechanical characteristics can be achieved without having to use additional/multiple layers, reinforcements (e.g., braids, coils, etc.), or the like along shaft 114. In addition, it may be possible to precisely direct the microwave radiation to target regions so that precise target regions shaft 114 are treated with microwave energy.

Figure 8:
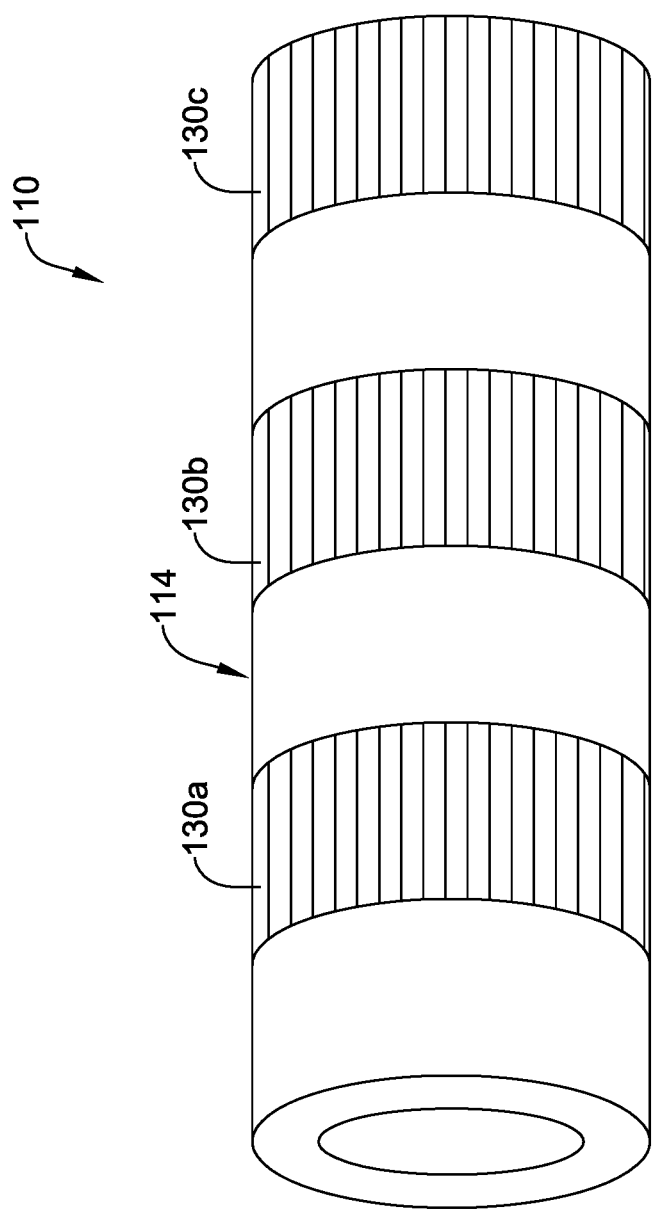
FIG. 8 schematically illustrates a portion of an example medical device.
Figure 9:
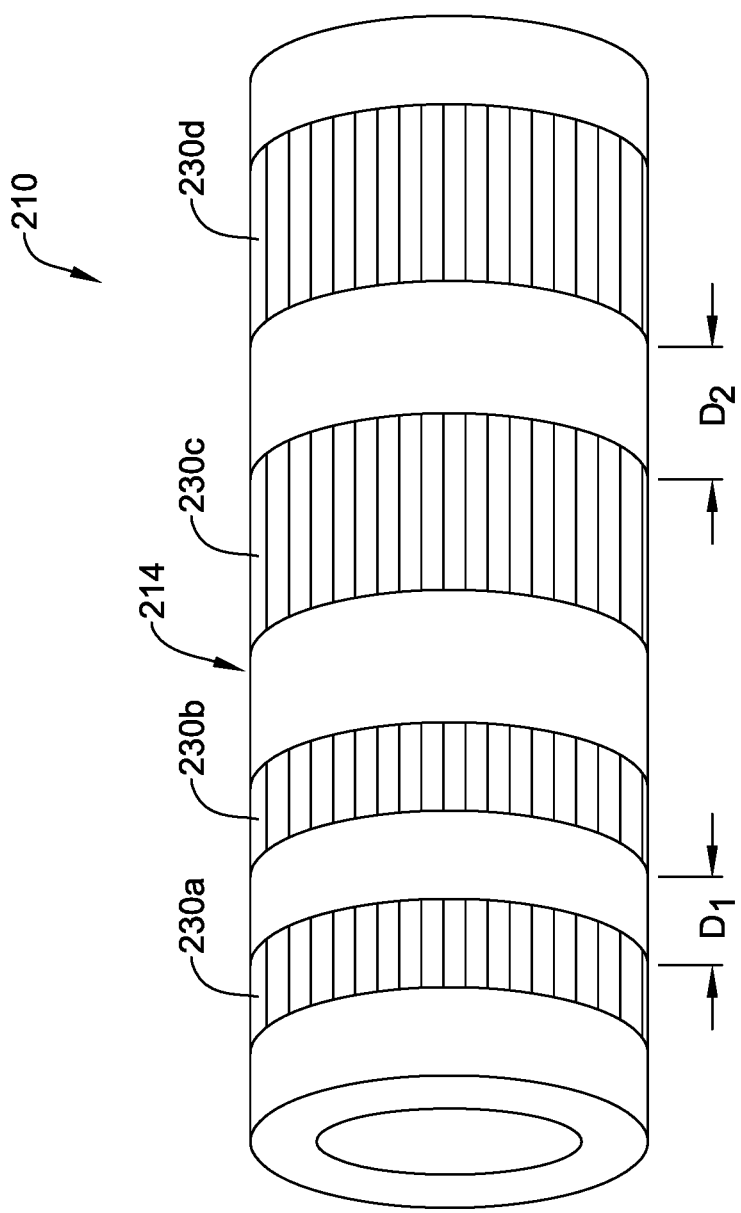
FIG. 9 schematically illustrates a portion of an example medical device.

FIG. 8 illustrates device 110 where a plurality of sections 130a/130b/130c along shaft 114 are locally treated with microwave radiation. In this example, three sections 130a/130b/130c treated with microwave radiation are shown. However, this is not intended to be limiting as more or fewer treated sections may be included. In addition, the treated sections 130a/130b/130c are shown as extending fully around the circumference of shaft 114, as having a constant length in the axial direction, and as being equally spaced from one another. This is also not intended to be limiting. Devices are contemplated where one or more of sections 130a/130b/130c span only a portion of the circumference of shaft 114. Furthermore, FIG. 9 illustrates another example device 210, which may be similar in form and function to other devices disclosed herein, that includes shaft 214. Shaft 214 may include treated sections 230a/230 and treated sections 230c/230d. In this example, sections 230a/230b have a length in the axial direction that is shorter than that of sections 230c/230d. Thus, shafts are contemplated where the axial length of treated sections can vary. Furthermore, sections 230a/230b are spaced a distance D1 from one another and sections 230c/230d are spaced a distance D2 from one another. In this example, distance D1 is shorter than distance D2. Thus, shafts are contemplated where the distance between treated sections can vary.

Figure 10:
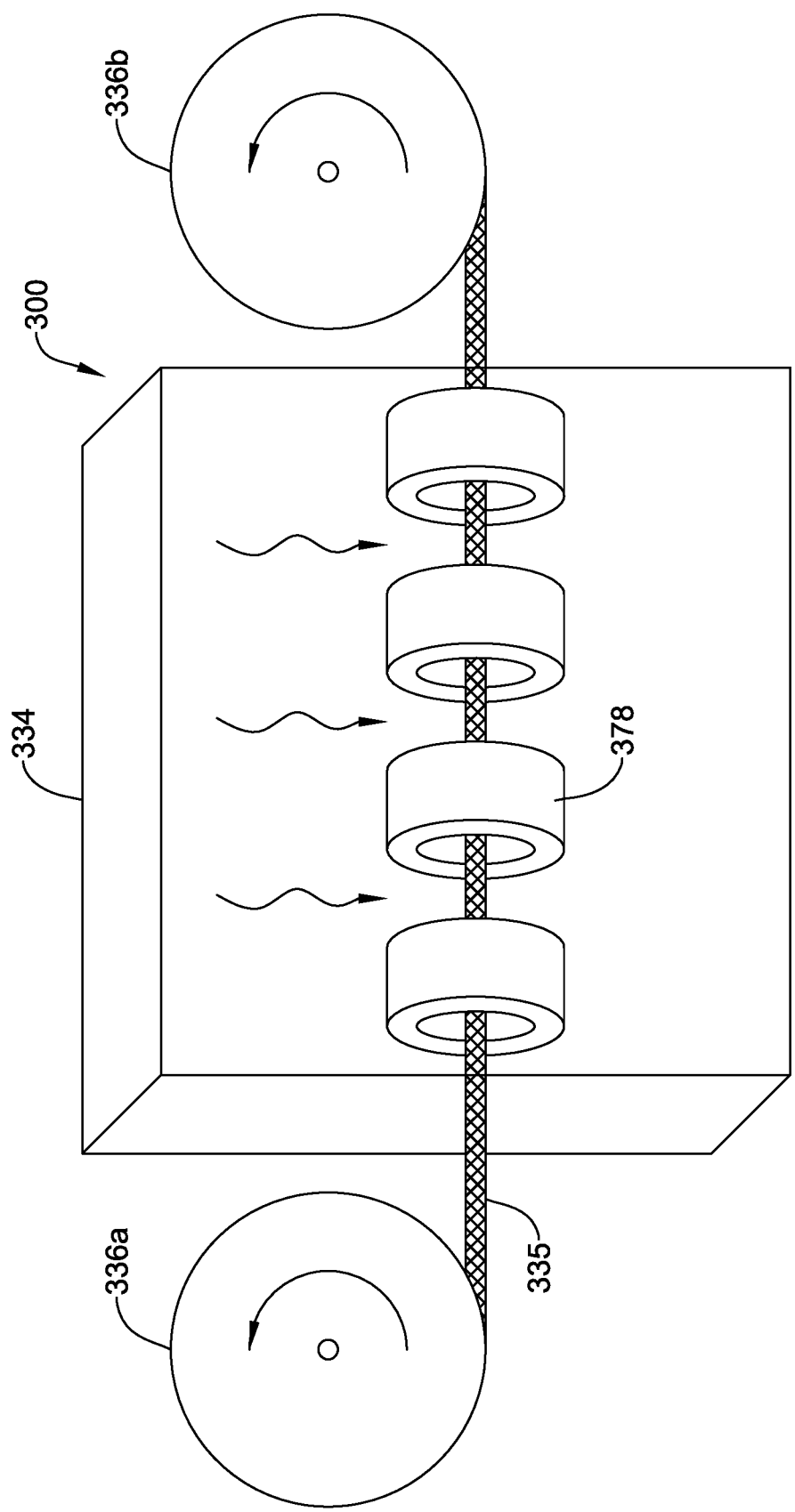
FIG. 10 schematically illustrates an example system.

FIG. 10 illustrates an example system 300 that may be used to manufacture at least some of the shafts/medical devices disclosed herein. For example, system 300 may include a microwave device 334 (e.g., a variable frequency microwave device). Tubing 335 may be fed through microwave device 334 using rollers 336a/336b. One or more shields 378 may be positioned within microwave device 334 to shield portions of tubing 335 from microwave energy. The process for using system 300 may include reeling tubing 335 into microwave device 334, exposing non-shielded portions of tubing 335 to microwave energy for a desired time period, and then reeling tubing 335 out of microwave device 334.

In some instances, a system may be used to focus the microwave energy precisely to preselected spatial sections on the device. Such systems may include using so-called near-field plates for subwavelength focusing, based on metamaterials. In general, near-field plates may take the form of a flat two-dimensional structure that can manipulate the amplitude, phase and polarization of transmitted electromagnetic fields at each point along the surface in the plate and configurations can be calculated to precisely generate resulting prescribed wavefronts at the device with subwavelength precision, similar to holographic optical elements as used for laser beam manipulation. In other words, alternative to shielding the field at certain sections of the device, the field strength can be manipulated by using these near-field plates. In some instances, near-field plates can be made by coating conductive copper patterns on microwave transparent polystyrene plates.

The materials that can be used for the various components of medical device 10 (and/or other devices disclosed herein) may include those commonly associated with medical devices. For simplicity purposes, the following discussion makes reference to medical device 10. However, this is not intended to limit the devices and methods described herein, as the discussion may be applied to other similar tubular members and/or components of tubular members or devices disclosed herein.

Medical device 10 and/or other components thereof may be made from a metal, metal alloy, polymer (some examples of which are disclosed below), a metal-polymer composite, ceramics, combinations thereof, and the like, or other suitable material. Some examples of suitable polymers (in addition to those disclosed herein) may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTEL- LOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method for drying a medical device, the method comprising:
    disposing a medical device within a drying apparatus;
    wherein the medical device includes a metallic stent or a polymeric stent;
    wherein the drying apparatus includes a variable frequency microwave heating device;
    wherein the medical device includes a substrate, the substrate including an active pharmaceutical ingredient and a solvent; and
    shielding one or more sections of the medical device;
    heating the medical device with the drying apparatus, wherein heating evaporates at least a portion of the solvent and results in crystal formation of at least a part of the active pharmaceutical ingredient, wherein the crystal formation has a substantially uniform crystal structure and results in molecules of the active pharmaceutical ingredient at least partially having a parallel alignment,
    wherein heating the medical device with the drying apparatus includes cycling the variable frequency microwave heating device across the frequency band.

2. The method of claim 1, wherein the medical device includes a metallic stent.

3. The method of claim 1, wherein the medical device includes a polymeric stent.

4. The method of claim 1, wherein the variable frequency microwave heating device is designed to heat across a frequency band of 300 MGz to 40 GHz.

5. The method of claim 1, wherein the cycling occurs at a fixed power input.

6. The method of claim 1, wherein the cycling occurs at a cycle time of 10-500 ms.

7. The method of claim 1, wherein the variable frequency microwave heating device monitors the temperature of the medical device and modulates the frequency based on the temperature of the medical device.

8. The method of claim 1, wherein the substrate includes poly-L-lactic acid, poly-D-lactic acid, a racemic mixture of poly-L-lactic acid and poly-D-lactic acid, poly(lactic-co-glycolic acid), or combinations thereof.

9. The method of claim 1, wherein the active pharmaceutical ingredient includes everolimus, paclitaxel, or combinations thereof.

10. The method of claim 1, wherein heating the medical device with the drying apparatus defines a plurality of hydrophilic regions along the substrate.

11. The method of claim 1, wherein heating the medical device with the drying apparatus forms a plurality of micro-channels in the substrate.

12. The method of claim 1, further comprising cooling a section of the medical device while heating the medical device within the drying apparatus.

13. The method of claim 1, further comprising covering a first region of the medical device with a shielding material.

14. The method of claim 13, wherein heating the medical device with the drying apparatus evaporates at least a second portion of the solvent from a second region of the medical device that is free of the shielding material.

15. A method for drying a medical device, the method comprising:
    disposing a medical device within a variable frequency microwave heating device, the medical device including a bioabsorbable stent with a coating;
    shielding one or more sections of the medical device;
    wherein the coating has a substantially uniform crystal structure;
    wherein the medical device includes a polymeric material and a solvent;
    heating the medical device with the variable frequency microwave heating device, wherein heating evaporates at least a portion of the solvent; and
    wherein heating the medical device with the variable frequency microwave heating device includes cycling the variable frequency microwave heating device across a frequency band, and cycling occurs at a fixed power input and occurs at a cycle time of 10-500 ms.

16. The method of claim 15, wherein the frequency band includes a frequency band of 300 MHz to 40 GHz.

17. The method of claim 15, wherein the coating includes one or more of a paclitaxel or everolimus.

18. The method of claim 15, wherein heating the medical device defines a plurality of hydrophilic regions within the coating of the stent.

19. The method of claim 15, wherein the coating has a plurality of micro-channels formed therein.

* * * * *